United States Patent [19]

Horst

[11] Patent Number: 5,152,300
[45] Date of Patent: Oct. 6, 1992

[54] GUARD FOR PROTECTING THE CORNER OF A PATIENT'S MOUTH

[76] Inventor: Patricia J. Horst, 2625 Harlem Blvd., Rockford, Ill. 61103

[21] Appl. No.: 783,539

[22] Filed: Oct. 28, 1991

[51] Int. Cl.$^5$ .............................................. A61C 5/14
[52] U.S. Cl. ..................................... 128/857; 433/93; 128/859
[58] Field of Search ............... 128/846, 857, 859, 861, 128/862; 433/93, 94, 91, 136, 137, 140

[56] References Cited

U.S. PATENT DOCUMENTS

| | | | |
|---|---|---|---|
| 364,505 | 6/1887 | Genese | 483/93 |
| 4,338,928 | 7/1982 | Martin et al. | 128/857 |
| 4,721,465 | 1/1988 | Barasz | 433/137 |
| 4,828,491 | 5/1989 | Gray | 433/136 |
| 4,971,557 | 11/1990 | Martin | 433/140 |
| 5,011,409 | 4/1991 | Gray | 433/137 X |

Primary Examiner—Robert A. Hafer
Assistant Examiner—Brian E. Hanlon
Attorney, Agent, or Firm—Leydig, Voit & Mayer

[57] ABSTRACT

The guard is made of soft flexible material and includes a pair of hinged wings adapted to be placed in straddling relation with the cheek of a dental patient. A forwardly facing and generally V-shaped throat is formed in the forward margins of the wings and cradles and cushions a dental instrument to prevent the instrument from causing sores in the corner of the patient's mouth.

7 Claims, 2 Drawing Sheets

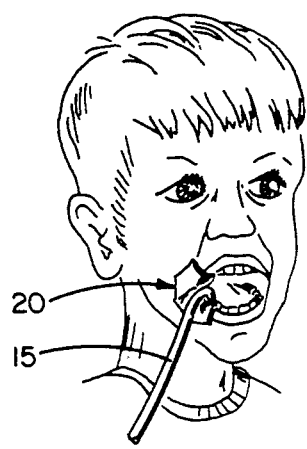
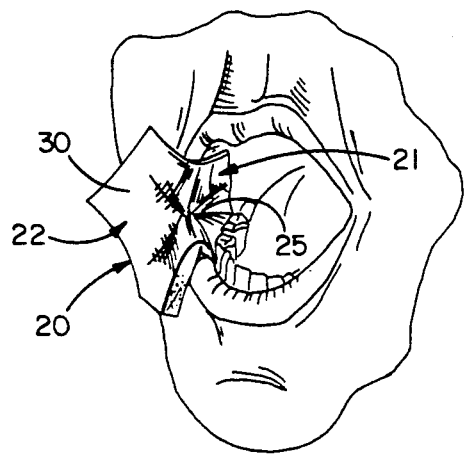
FIG. 1
FIG. 2
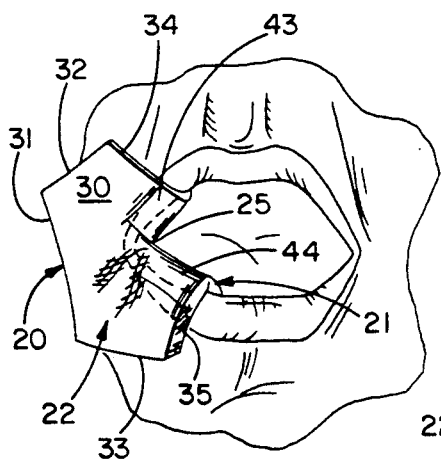
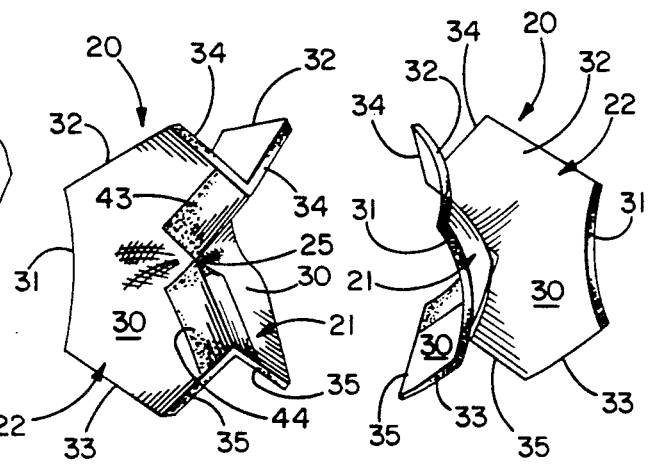
FIG. 3
FIG. 4
FIG. 5
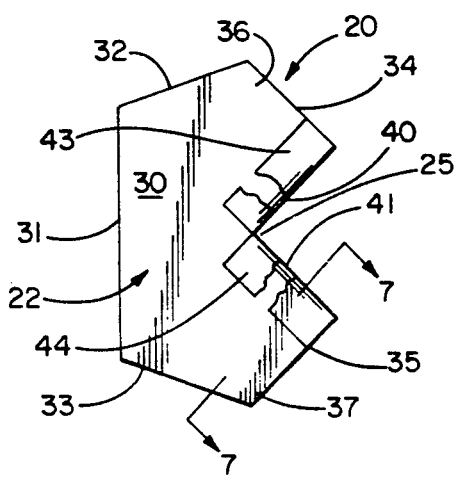
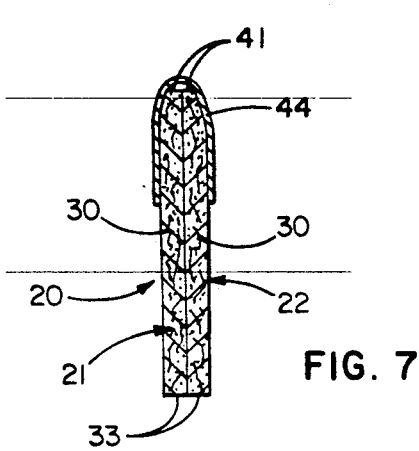
FIG. 6
FIG. 7

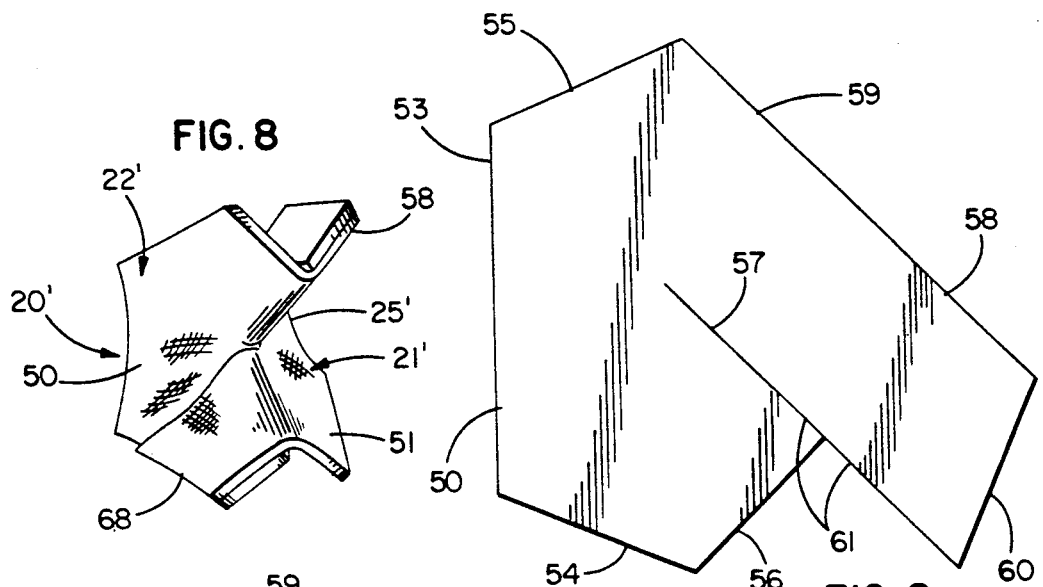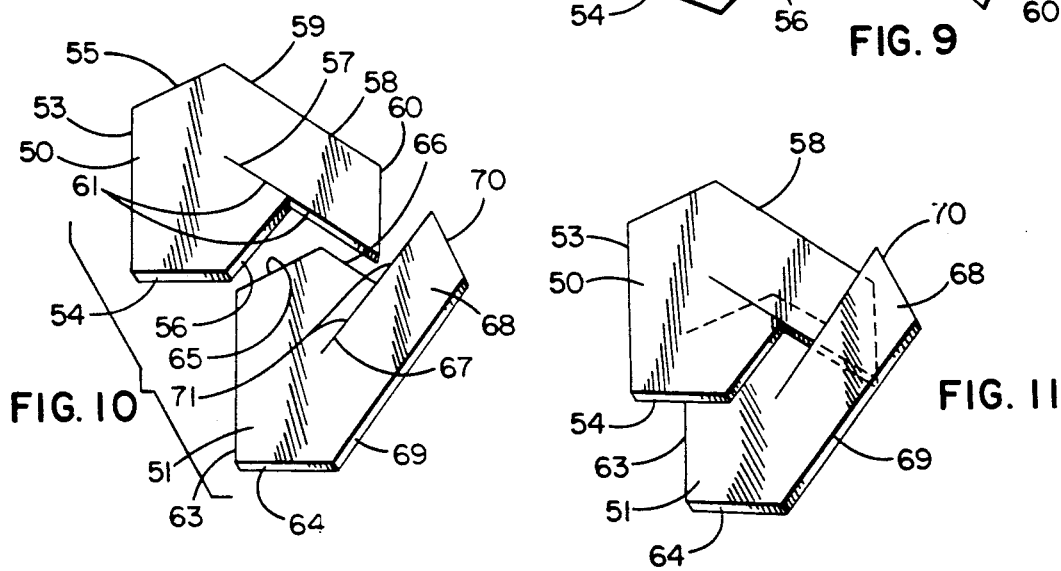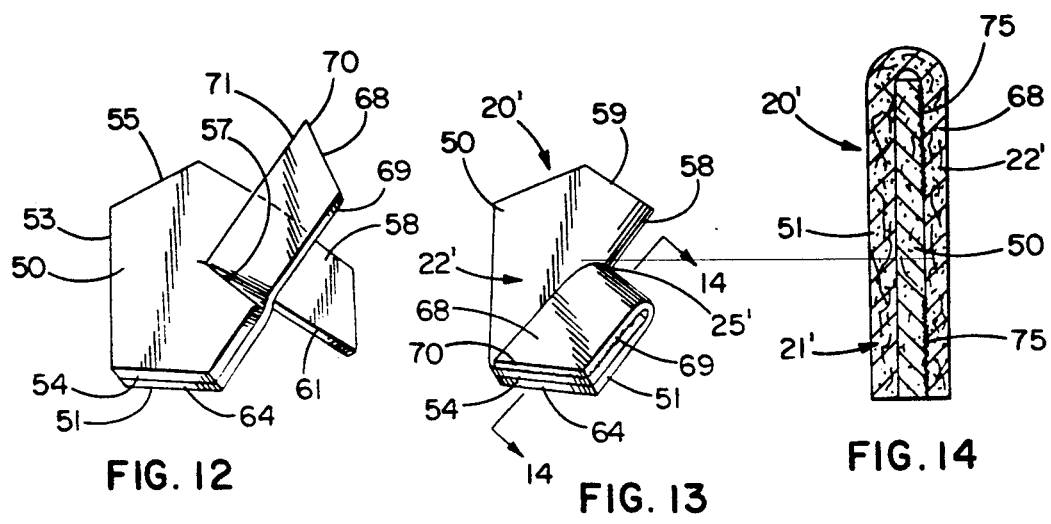

5,152,300

GUARD FOR PROTECTING THE CORNER OF A PATIENT'S MOUTH

BACKGROUND OF THE INVENTION

One of the most common patient complaints involving dental procedures is the constant irritation of the corners of the patient's mouth by saliva extractors and other dental instruments. When, for example, a saliva extractor is hung in the corner of the mouth for a significant period of time, the rubbing and pressure can cause small splits that may take days or even weeks to heal. Other dental instruments pressing against the corners of the mouth also may irritate the corners and cause painful and difficult-to-heal sores. Medical instruments used during medical procedures can result in similar problems.

SUMMARY OF THE INVENTION

The general aim of the present invention is to provide a new and improved guard which may be easily and securely placed in the mouth to protect the corner thereof from irritation otherwise resulting from dental instruments or medical instruments.

A more detailed object of the invention is to achieve the foregoing by providing a guard having a pair of soft flexible wings adapted to straddle the cheek adjacent the corner of the mouth and formed with a throat for cradling the instrument and for establishing a cushion between the instrument and the corner of the mouth.

A further object of the invention is to provide a guard which provides little or no interference with the dental procedure being performed, which clings to the inner and outer sides of the cheek, and which flexes vertically as the mouth is opened and closed.

The invention also resides in the economical formation of the guard from two identical pieces of soft and flexible material and in the manner of securing the pieces together to form a pair of hinged wings which define an instrument-receiving throat.

These and other objects and advantages of the invention will become more apparent from the following detailed description when taken in conjunction with the accompanying drawings.

BRIEF DESCRIPTION OF THE DRAWINGS

FIG. 1 is a perspective view showing one embodiment of a new and improved guard of the invention in the mouth of a dental patient and showing the guard protecting the corner of the mouth against irritation by a typical dental instrument.

FIG. 2 is an enlarged perspective view showing the guard in the mouth from a different angle and without the dental instrument.

FIG. 3 is a view generally similar to FIG. 2 but shows the guard as seen directly from in front of the patient's face.

FIG. 4 is an enlarged perspective view of the guard of FIG. 3 as seen from the front thereof.

FIG. 5 is a perspective view of the guard of FIG. 3 as seen from the rear thereof.

FIG. 6 is a side elevational view of the guard shown in FIGS. 3 to 5.

FIG. 7 is an enlarged cross-section taken along the line 7—7 of FIG. 6.

FIG. 8 is a view similar to FIG. 4 but shows another embodiment of a mouth corner guard incorporating the unique features of the present invention.

FIG. 9 is an enlarged side elevational view of one of the two pieces of material used to make the corner guard of FIG. 8.

FIGS. 10, 11, 12 and 13 are perspective views schematically showing successive steps of assembling the two pieces of material in order to make the corner guard of FIG. 8.

FIG. 14 is an enlarged cross-section taken along the line 14—14 of FIG. 13.

DETAILED DESCRIPTION OF THE PREFERRED EMBODIMENT

FIG. 1 of the drawings shows a dental patient with a dental instrument 15 (herein, a saliva extractor) in one corner of his mouth. As is well known, if an instrument such as the extractor 15 is allowed to hang from the corner of the mouth for any significant period of time, the weight of the extractor together with the rubbing thereof against the moist corner can cause slits or other sores to develop in the corner at and near the area of contact. Sores of this type can be painful and may not heal for many days.

The present invention contemplates the provision of a unique guard 20 which fits securely in the mouth to cradle and cushion the instrument 15 and to prevent the instrument from rubbing against and irritating the corner of the mouth. The corner guard 20 of the invention is particularly characterized in that it clings securely but comfortably in the mouth, provides a cradle for the instrument, flexes readily when the mouth is opened and closed, and presents very little obstruction to the dental operation being performed.

In general, the guard 20 comprises inner and outer wings 21 and 22 adapted to straddle the patient's cheek adjacent one corner of the mouth and adapted to lie along and cling to the inner and outer sides, respectively, of the cheek. The forward margins of the two wings are shaped to define a forwardly facing and substantially V-shaped throat 25 which forms a cradle for the instrument 15, the apex of the throat being located substantially at the corner of the mouth. In addition, the V-shaped throat promotes vertical flexure of the guard 20 and allows the patient to freely open and close his mouth while the guard is in place.

Although the corner guard could be of one-piece molded construction, in the embodiment of the corner guard 20 specifically shown in FIGS. 1 to 7, the wings 21 and 22 are made of two separate but identical pieces or halves 30 of soft and flexible material such as embossed and reinforced non-woven paper cloth backed by a very thin plastic sheet. While various soft and flexible materials such as cotton, paper, foam or plastic may be used, the preferred material is one sold under the trade designator MICRODON. The material has a thickness of approximately 0.040" and need not necessarily be absorbent as long as it is soft and flexible.

Each of the halves 30 for making the wings 21 and 22 includes an upright rear edge 31 (FIG. 6), a back upper edge 32 extending upwardly and forwardly from the upper end of the rear edge 31 at an obtuse angle relative thereto, and a back lower edge 33 extending downwardly and rearwardly from the lower end of the rear edge 31 at the same obtuse angle. A front upper edge 34 extends downwardly and forwardly from the upper end of the back upper edge 32 while a front lower edge 35 extends upwardly and forwardly from the lower end of the back lower edge 33. As a result of this arrangement, each of the halves 30 is formed with an upper generally triangular portion 36 and with a lower generally triangular portion 37.

In carrying out the invention, the forward margin of each of the halves 30 is formed with a forwardly opening and generally V-shaped notch. When the two halves 30 are assembled to form the wings 21 and 22, the notches in the two halves coact to form the V-shaped throat 25 of the guard 20. Herein, each notch includes an upper edge 40 (FIG. 6) which extends downwardly and rearwardly from the lower end of the front upper edge 34. In addition, each notch includes a lower edge 41 which extends upwardly and rearwardly from the upper end of the front lower edge 35. The two edges 40 and 41 of each notch are disposed substantially perpendicular to one another, each edge being inclined approximately at a 45 degree angle.

The two halves 30 are assembled by superimposing the halves in face-to-face relation with the halves located such that the edges 31 to 35 and the edges 40 and 41 of each half are aligned with the corresponding edges of the other half. Upper and lower flexible connectors 43 and 44 then are used to secure the halves to one another. In the embodiment of FIGS. 1 to 7, each of the connectors is in the form of a strip of tape having pressure sensitive adhesive on one side thereof. The upper tape 43 is folded around the upper edges 40 of the V-shaped notches and is adhesively secured to the outboard sides of the two halves 30. Similarly, the lower tape 44 is folded around the lower edges 41 of the notches and also is secured to the outboard sides of the two halves (see FIG. 7).

Thus, the upper and lower tapes 43 and 44 join the two identical halves 30 to one another so as to form the wings 21 and 22. In addition, the tapes define hinges permitting the wings to be spread apart and placed in straddling relation with the patient's cheek. Finally, the two tapes 43 and 44 define the surfaces of the throat 25 and are the surfaces which are actually engaged by the instrument 15.

The corner guard 20 is used by spreading the wings 21 and 22 as permitted by the tapes 43 and 44 and placing the wings in straddling relation with the patient's cheek while crowding the wings rearwardly such that the apex of the throat 25 is against or closely adjacent the corner of the mouth. Thus, the wing 21 lies inside of the cheek while the wing 22 lies outside of the cheek. The V-shaped throat 25 conforms generally to the shape of the corner of the mouth and defines a cradle for receiving the instrument 15. Because the material of the guard 20 is soft, it forms a cushion between the instrument and the corner of the mouth and reduces irritation otherwise caused by the instrument pressing on and rubbing against the corner.

As shown in FIG. 2, the inner wing 21 of the guard 20 is located between the inner side of the patient's cheek on the one hand and between the adjacent teeth and gums on the other hand. Thus, the guard is held securely in place and is held away from the tongue and from the area where the dental operation is being performed. In addition, the outer wing 22 tends to spring inwardly against the outer side of the cheek and also helps hold the guard in place.

The V-shaped throat 25 also imparts vertical flexibility to the guard 20 and allows the wings 21 and 22 to flex Vertically about the apex of the throat as the patient's mouth is opened and closed. When the patient closes and then opens his mouth, the resilient memory of the material of the guard tends to cause the wings to return vertically to their original positions.

A modified guard 20' is shown in FIGS. 8 to 14 and is identical in function and similar in overall structure to the guard 20 of the first embodiment in that the guard includes inner and outer wings 21' and 22' and a forwardly facing and generally V-shaped throat 25'. The guard 20', however, does not require tapes similar to the tapes 43 and 44 of the first embodiment and lends itself to a more automated and higher speed assembly process.

More specifically, the guard 20' is formed by two soft and flexible pieces or halves 50 and 51 which are identical in shape but which are located in different orientations during assembly. The half 50 is shown in FIG. 9 and includes a body with an upright rear edge 53, a lower edge 54 extending downwardly and forwardly from the lower end of the rear edge, and an upper edge 55 extending upwardly and forwardly from the upper end of the rear edge. In addition, the half 50 includes a front edge 56 extending upwardly and forwardly from the lower end of the lower edge 54 and further includes an edge 57 extending upwardly and rearwardly from the forward end of the front edge 57.

The half 50 is completed by a projecting tab 58 integral with the body and having a top edge 59 extending downwardly and forwardly from the upper end of the upper edge 55. In addition, the tab 58 includes a forward edge 60 extending downwardly from the lower end of the top edge 59 and further includes a bottom edge 61 extending upwardly and rearwardly from the lower end of the forward edge 60. The bottom edge 61 of the tab 58 intersects the front edge 56 of the body at right angles and continues rearwardly past such edge in parallel relation with the edge 57. In effect, the edge 57 and the upper rear portion of the edge 61 form a slit in the half 50 and indeed are formed by slitting the half 50.

The half 51 is identical in size and shape to the half 50 but, prior to final assembly, is inverted 180 degrees relative to the half 50 about a horizontal axis disposed in the plane of the paper. Thus, the half 51 includes a body with an upright rear edge 63 (FIG. 10), a lower edge 64 extending downwardly and forwardly from the lower end of the rear edge, and an upper edge 65 extending upwardly and forwardly from the upper end of the rear edge. Moreover, the half 51 includes a front edge 66 extending downwardly and forwardly from the upper end of the upper edge 65 and further includes an edge 67 extending downwardly and rearwardly from the forward end of the front edge 66.

As shown most clearly in FIG. 10, the half 51 also includes a projecting tab 68 integral with the body and having a bottom edge 69 extending upwardly and forwardly from the lower end of the lower edge 64, a forward edge 70 extending upwardly from the bottom edge 69, and a top edge 71 extending downwardly and rearwardly from the upper end of the forward edge 70. The top edge 71 intersects the front edge 66 at 90 degrees and continues rearwardly past such front edge in parallel relation with the edge 67 so that, in effect, a slit is defined between the edges 67 and 71.

Assembly of the halves 50 and 51 is effected by orienting the halves relative to one another as shown in FIG. 10 such that the tab 58 extends downwardly while the tab 68 extends upwardly. The two halves then are slid edgewise into face-to-face relation and are located such that the edges 53, 54 and 55 of the half 50 are aligned with the edges 63, 64 and 65 of the half 51. As an incident to sliding the halves into face-to-face relation, the tab 58 is slipped into the slit between the edges 67 and 71 while the tab 68 is slipped into the slit between the edges 57 and 61. The tab 58 then is folded over the edge 67 and against the outboard side of the half 51 and is bonded to such outboard side either by one or more spots of adhesive or by heat sealing. Similarly, the tab 68 is folded over the edge 57 and is bonded to the outboard side of the half 50 by adhesive or heat sealing. The bond between the tab 68 and the outboard side of the half 50 is shown schematically in FIG. 14 and is designated as 75.

Once the tabs 58 and 68 have been bonded, the half 50 and the tab 68 form the wing 22' while the half 51 and the tab 58 form the wing 21'. The folded portions of the tabs define hinges permitting the wings to be spread apart and, in addition, the folded portions of the tabs define the surfaces of the V-shaped throat 25' for receiving the instrument 15.

While the invention has been described specifically in connection with a dental procedure, it should be appreciated that the guard 20, 20' may be used equally well in medical procedures to protect the corner of the patient's mouth from medical instruments.

I claim:

1. A guard for helping prevent an instrument from injuring the corner of a patient's mouth during a dental or medical procedure; said guard being made of soft and flexible material and comprising inner and outer wings adapted to straddle the patient's cheek adjacent said corner and to lie along the inner and outer sides, respectively, of the cheek, each of said wings having a free rear edge port having a forward margin, the forward margins of said wings being joined to one another in such a manner a permit the wings to be spread away from one another placed in straddling relation with the patient's check and a substantially V-shaped and forwardly facing throat in the forward margins of said wings for receiving the instrument, said throat having upper and lower sides which converge an apex located substantially at said corner.

2. A guard as defined in claim 1 in which each of said wings includes inboard and outboard sides and is formed by a separate flat piece of said material, each of said pieces including a forward edge formed with a generally V-shaped and forwardly opening notch having upper and lower edges, said pieces being identical and being superimposed in face-to-face relation with the notch in each piece disposed in alignment with the notch in the other piece so as to define said throat, an upper flexible connector secured to the outboard sides of said wings and extending around the upper edges of said notches, and a lower flexible connector secured to the outboard sides of said wings and extending around the lower edges of said notches, said connectors joining said wings to one another and flexing to permit said wings to be spread away from one another and placed in straddling relation with the patient's cheek.

3. A guard as defined in claim 2 in which each of said connectors comprises a piece of flexible material adhered to the outboard sides of said wings and folded around the respective edges of said notches.

4. A guard as defined in claim 3 in which each of said connectors is a strip of pressure sensitive tape.

5. A guard as defined in claim 2 in which each of said flat pieces includes (a) an upright rear edge, (b) back upper and back lower edges extending forwardly from said rear edge at substantially equal obtuse angles, (c) a front upper edge extending downwardly and forwardly from said back upper edge and joining the upper edge of said notch, and (d) a front lower edge extending upwardly and forwardly from said back lower edge and joining the lower edge of said notch.

6. A guard as defined in claim 1 in which said wings are formed by first and second identically shaped but differently oriented flat pieces of material having first and second tabs, respectively, said first tab being folded over and bonded to said second piece, said second tab being folded over and bonded to said first piece, the bonding of said tabs to said pieces joining said wings and permitting the wings to be spread away from one another, said throat being defined by portions of said tabs.

7. A guard as defined in claim I in which said wings are formed by first and second identically shaped but differently oriented flat pieces of said material, each of said pieces having (a) an upright rear edge, (b) a lower edge extending downwardly and forwardly from the lower end of said rear edge, and (c) an upper edge extending upwardly and forwardly from the upper end of said rear edge, said first piece including a front edge extending upwardly and forwardly from the lower end of the lower edge of said first piece and further including an additional edge extending upwardly and rearwardly from the forward end of said front edge, said first piece including an integral first tab having (a) a top edge extending downwardly and forwardly from the upper end of the upper edge of said first piece, (b) a forward edge extending downwardly from said top edge, and (c) a bottom edge extending upwardly and rearwardly from the lower end of said forward edge, the bottom edge of said tab intersecting said front edge and continuing rearwardly past said front edge in parallel relation with said additional edge, said second piece including a front edge extending downwardly and forwardly from the upper end of the upper edge of said second piece and also including a further edge extending downwardly and rearwardly from the forward end of the front edge of the second piece, said second piece including an integral second tab having (a) a bottom edge extending upwardly and forwardly from the lower end of the lower edge of said first piece, (b) a forward edge extending upwardly from the upper end of the bottom edge and (c) a top edge extending downwardly and rearwardly from the upper end of the forward edge of the second tab, the top edge of said second tab intersecting the front edge of said second piece and continuing rearwardly past such front edge in parallel relation with said further edge, portions of said first and second pieces being in face-to-face relation and located with said rear edges in alignment with one another, with said lower edges in alignment with one another and with said upper edges in alignment with one another, said first tab being folded over and bonded to said second piece and being located with its top edge in alignment with the front edge of the second piece and with its forward edge in alignment with the upper edge of the second piece, said second tab being folded over and bonded to said first piece and being located with its bottom edge in alignment with the front edge of the first piece and with its forward edge in alignment with the lower edge of the first piece.

* * * * *